(12) United States Patent
Singh et al.

(10) Patent No.: US 12,090,466 B2
(45) Date of Patent: Sep. 17, 2024

(54) CATALYSTS FOR THE DEOXYGENATION OF ESTERS OF FREE FATTY ACIDS AND TRIGLYCERIDES

(71) Applicant: SBI BioEnergy, Edmonton (CA)

(72) Inventors: Inder Pal Singh, Edmonton (CA); Shradha Singh, Edmonton (CA); Bharat Mistry, Edmonton (CA); Zhiyong Li, Edmonton (CA)

(73) Assignee: SBI BioEnergy, Edmonton (CA)

( * ) Notice: Subject to any disclaimer, the term of this patent is extended or adjusted under 35 U.S.C. 154(b) by 548 days.

(21) Appl. No.: 17/431,187

(22) PCT Filed: Feb. 12, 2020

(86) PCT No.: PCT/CA2020/050183
§ 371 (c)(1),
(2) Date: Aug. 16, 2021

(87) PCT Pub. No.: WO2020/168418
PCT Pub. Date: Aug. 27, 2020

(65) Prior Publication Data
US 2022/0184581 A1    Jun. 16, 2022

Related U.S. Application Data

(60) Provisional application No. 62/807,300, filed on Feb. 19, 2019.

(51) Int. Cl.
*B01J 23/00* (2006.01)
*B01J 23/10* (2006.01)
(Continued)

(52) U.S. Cl.
CPC ............ *B01J 23/002* (2013.01); *B01J 23/10* (2013.01); *B01J 35/40* (2024.01); *B01J 35/613* (2024.01);
(Continued)

(58) Field of Classification Search
CPC ... C07C 1/2078; C07C 1/213; C07C 2521/06; C07C 2523/06; C07C 2523/10;
(Continued)

(56) References Cited

U.S. PATENT DOCUMENTS 8,053,615 B2    11/2011  Cortright et al.
8,366,907 B2 *  2/2013   Hallen .................. B01J 21/066
                                                  585/737
(Continued)

FOREIGN PATENT DOCUMENTS

WO    2009046636       4/2009
WO    2011012440       2/2011
WO    WO-2019084657 A1 *  5/2019  ............... C10G 3/47

OTHER PUBLICATIONS

Kay Lup Andrew Ng et al: "A review on reactivity and stability of heterogeneous metal catalysts for deoxygenation of bio-oil model compounds", Journal of Industrial and Engineering Chemistry, The Korean Society of Industrial and Engineering Chemistry, Korea vol. 56, Jul. 4, 2017 (Jul. 4, 2017), pp. 1-34, XP085213867, ISSN: 1226-086X, DOi: 10.1016/J.JIEC.2017.06.049.

*Primary Examiner* — Patricia L. Hailey
(74) *Attorney, Agent, or Firm* — Norton Rose Fulbright Canada (57) ABSTRACT

It is provided solid, heterogeneous catalysts for the deoxygenation of esters of free fatty acids and triglycerides, and for the production of hydrocarbons that can be used as biofuels. More particularly, the catalyst comprises at least one metal oxide, the catalyst having a formula $Al_aCu_bNi_cSi_dTi_eZn_fZr_gLa_hCe_iW_jSn_kGa_lFe_mMO_nMn_oCO_pO_x$, wherein a, b, c, d, g, h, i, j, k, l, m n, o, p and x are the molar ratios of the respective elements, wherein a, b, c, d, h, i, j, k, l, m, n, o and p are >0, e, f and g are >0 and x is such that the catalyst is electrically neutral.

21 Claims, 6 Drawing Sheets

(51) Int. Cl.
- *B01J 35/40* (2024.01)
- *B01J 35/61* (2024.01)
- *B01J 35/63* (2024.01)
- *B01J 37/04* (2006.01)
- *B01J 37/08* (2006.01)
- *C07C 1/207* (2006.01)
- *C07C 1/213* (2006.01)

(52) U.S. Cl.
CPC .............. *B01J 35/633* (2024.01); *B01J 37/04* (2013.01); *B01J 37/08* (2013.01); *C07C 1/2078* (2013.01); *C07C 1/213* (2013.01); *C07C 2521/06* (2013.01); *C07C 2523/06* (2013.01); *C07C 2523/10* (2013.01)

(58) Field of Classification Search
CPC ...... B01J 23/002; B01J 35/613; B01J 35/633; B01J 35/40; B01J 23/10; B01J 37/04; B01J 37/08; B01J 35/615; B01J 35/655
USPC ................................. 502/107, 300, 302–355
See application file for complete search history.

(56) References Cited

U.S. PATENT DOCUMENTS

| | | | |
|---|---|---|---|
| 8,507,400 B2* | 8/2013 | Nguyen | B01J 8/0457 |
| | | | 205/267 |
| 10,155,908 B2* | 12/2018 | Dayton | B01J 35/31 |
| 2008/0216391 A1 | 9/2008 | Cortright et al. | |
| 2012/0283459 A1 | 11/2012 | Manhoe et al. | |
| 2012/0305836 A1* | 12/2012 | Traynor | C10G 65/04 |
| | | | 252/182.12 |
| 2013/0190535 A1* | 7/2013 | Jackson | B01J 23/83 |
| | | | 568/397 |
| 2015/0166901 A1* | 6/2015 | Traynor | B01J 23/883 |
| | | | 502/309 |
| 2015/0183701 A1* | 7/2015 | Blank | B01J 37/0207 |
| | | | 568/903 |
| 2016/0108330 A1* | 4/2016 | Cortright | C10G 3/46 |
| | | | 585/16 |

* cited by examiner

CATALYSTS FOR THE DEOXYGENATION OF ESTERS OF FREE FATTY ACIDS AND TRIGLYCERIDES

CROSS-REFERENCE TO RELATED APPLICATIONS

The present application a U.S. National Phase of International Application No. PCT/CA2020/050183, filed on Feb. 12, 2020, and claims benefit of U.S. Provisional Application No. 62/807,300 filed Feb. 19, 2019, the content of which is hereby incorporated by reference in its entirety.

FIELD OF THE INVENTION

The present disclosure generally relates to the production of biofuels. More particularly, the present disclosure relates to solid, heterogeneous catalysts for the deoxygenation of esters of free fatty acids and triglycerides.

BACKGROUND

Biofuels or renewable fuels provide a cleaner, low carbon alternative to non-renewable petroleum-derived transportation fuels. Various catalysts and processes have been developed and reported in the literature to convert naturally-occurring feedstock material (i.e., starting material) to hydrocarbon products. Such processes provide an alternative to petroleum-based transportation fuels.

The feedstock material may be obtained from plant oils, animal fats and the likes and may include processed or unprocessed vegetable oils or animal fats, such as esters of free fatty acids, triglycerides, diglycerides, monoglycerides, free fatty acids, carboxylic acids, and tall oils and mixtures thereof.

U.S. Pat. No. 9,206,367 describes the deoxygenation of oxygenated feed oils in the absence of a catalyst under vacuum or high hydrogen pressure and high temperatures. This process produces high percentage of residues or coke which causes significant molecular loss. Majority of feed oil remains unreacted or converted to unviable byproducts and hydrocarbon selectivity was less than 30%.

Other processes use hydrocracking or hydrotreating catalysts in the presence of hydrogen for the deoxygenation of the naturally-occurring feedstock material.

U.S. Pat. No. 8,366,907 describes a biofuel production process via decarboxylation and decarbonylation of natural oils using supported noble metal (platinum—Pt) catalysts. Pt supported on various supports is known to be an effective hydrocracking catalyst. However, platinum is known to be very sensitive to the presence of carbon monoxide and sulfur, which is generated during the decarboxylation process, such carbon monoxide causing catalyst poisoning (i.e., the partial or total deactivation of the catalyst). Pt-based catalysts are also known to produce coke deposits on the surface of the catalyst, thereby blocking the active sites, specifically in the absence of high-pressure hydrogen (Reaction Kinetics and Catalysis Letters; March 1980, Volume 13, Issue 1, pp 77-81).

U.S. Pat. Nos. 8,889,933 and 7,459,597 disclose hydrotreating and hydro-isomerization of renewable feedstocks in presence of a large quantity of hydrogen to produce hydrocarbons. However, the hydrotreating catalysts described therein are not stable in presence of water, which is co-produced during the hydro-deoxygenation of plant oils and animal fats. Also, the heat released during such hydrotreating reactions is a significant challenge for reactor design.

The deoxygenation catalysts known in the art therefore suffer from several shortcomings such as poor stability, low activity, undesirable side reactions, and/or a need to operate under high pressure conditions in the presence of hydrogen, hydrogen being generally produced from methane or natural gas or coal and being accordingly associated with a high energy intensity and a large carbon footprint. There is accordingly still a need to provide catalysts for deoxygenation reactions that do not exhibit or reduce the shortcomings discussed above.

SUMMARY

In accordance with one aspect of the disclosure, there is provided a catalyst comprising at least one metal oxide, the catalyst having a formula $Al_aCu_bNi_cSi_dTi_eZn_fZr_gLa_hCe_iW_jSn_kGa_lFe_mMo_nMn_oCo_pO_x$, wherein a, b, c, d, e, f, g, h, i, j, k, l, m, n, o, p and x are the molar ratios for the respective elements, wherein a, b, c, d, h, i, j, k, l, m, n, o and p are ≥0, e, f and g are >0 and x is such that the catalyst is electrically neutral.

In accordance with another aspect of the disclosure, there is provided a catalyst comprising at least one metal oxide, the catalyst having a formula $Al_aCu_bNi_cSi_dTi_eZn_fZr_gLa_hCe_iW_jSn_kGa_lFe_mMo_nMn_oCo_pO_x$, wherein a, b, c, d, e, f, g, h, i, j, k, l, m, n, o, p and x are the molar ratios for the respective elements, wherein a, b, c, d, e, h, i, j, k, l, m, n, o and p are ≥0, 0.38≤f≤2.74, 0.13≤g≤3.42 and x is such that the catalyst comprising the at least one metal oxide is electrically neutral.

In accordance with another aspect of the disclosure, there is provided a method for performing a deoxygenation reaction of a starting material comprising contacting the starting material with at least one catalyst comprising at least one metal oxide, wherein the at least one catalyst has a formula $Al_aCu_bNi_cSi_dTi_eZn_fZr_gLa_hCe_iW_jSn_kGa_lFe_mMo_nMn_oCo_pO_x$, wherein a, b, c, d, e, f, g, h, i, j, k, l, m, n, o, p and x are the molar ratios for the respective elements, wherein a, b, c, d, h, i, j, k, l, m, n, o and p are ≥0, e, f and g are >0 and x is such that the at least one catalyst is electrically neutral.

In accordance with another aspect of the disclosure, there is provided a method for performing a deoxygenation reaction of a starting material comprising contacting the starting material with at least one catalyst comprising at least one metal oxide, wherein the at least one catalyst has a formula $Al_aCu_bNi_cSi_dTi_eZn_fZr_gLa_hCe_iW_jSn_kGa_lFe_mMo_nMn_oCo_pO_x$, wherein a, b, c, d, e, f, g, h, i, j, k, l, m, n, o, p and x are the molar ratios for the respective elements, wherein a, b, c, d, e, h, i, j, k, l, m, n, o and p are ≥0, 0.38≤f≤2.74, 0.13≤g≤3.42 and x is such that the catalyst comprising the at least one metal oxide is electrically neutral.

In an embodiment, a, b, c, d, h, i, j, k, l, m, n, o and p are =0.

In another embodiment, 0.39≤e≤2.79.

In a further embodiment, 0.38≤f≤2.74.

In a further embodiment, 0.13≤g≤3.42.

In an embodiment, b≥0, c≥0, e>0, f>0 and g>0.

In another embodiment, a, d, h, i, j, k, l, m, n, o and p are =0.

In another embodiment, 0≤b≤1.04.

In an embodiment, 0≤c≤1.08.

In an embodiment, 0.39≤e≤2.79.

In another embodiment, 0.38≤f≤2.74.

In a further embodiment, 0.13≤g≤3.42.

In an embodiment, the at least one metal oxide is selected from the group consisting of Groups IIIA, IVA, IB, IIB, IIIB, IVB, VIB, VIIB and VIIIB.

In another embodiment, the catalyst is substantially free of any one of Pd, Pt, Ru, Ir, and Rh.

In a further embodiment, the catalyst has a surface area between about 10 m$^2$/g and about 500 m$^2$/g.

In an embodiment, the catalyst has a total pore volume between about 0.01 mL/g and about 1 mL/g.

In another embodiment, the catalyst is in powdered, pelleted, extruded form or coated on a metal or any suitable surface with or without an added binder.

In an embodiment, the catalyst is calcined.

In an embodiment, the starting material comprises triglycerides, diglycerides, monoglycerides, fatty acids, esters of fatty acids, biomass derived biooils, ketone, alcohol or a combination thereof.

In another embodiment, the starting material is vegetable oil, used cooking oil, derived from animal fat, tall oil or any combination thereof.

In a particular embodiment, the starting material is vegetable oil.

In another embodiment, the starting material is used cooking oil.

In another embodiment, the starting material is derived from animal fat.

In a further embodiment, the starting material is tall oil.

In an embodiment, the starting material is diluted with a hydrocarbon or co-fed with a hydrocarbon or methanol or water or a hydrogen donor.

In an embodiment, the hydrogen donor is formic acid, methyl formate, methanol, ethanol, propanol, butanol, or any other suitable hydrogen donor agents or any combination thereof.

In an embodiment, the deoxygenation reaction is conducted in the absence of added hydrogen.

In an embodiment, the deoxygenation reaction is conducted at a temperature between about 250° C. and about 500° C.

In an embodiment, the deoxygenation reaction is conducted at a temperature between about 350° C. and about 425° C.

In an embodiment, the deoxygenation reaction is conducted at a pressure between about ambient pressure and about 5,000 psi.

In an embodiment, the deoxygenation reaction is conducted at a pressure between about 750 psi and about 2,500 psi.

In an embodiment, the deoxygenation reaction is conducted at a weight hourly space velocity between about 0.09 hr$^{-1}$ and about 3 hr$^{-1}$.

In an embodiment, at least one hydrocarbon product is produced.

In a further embodiment, the at least one hydrocarbon product comprises one or more of alkanes, iso-alkanes, cycloalkanes, cycloolefins, aromatics, alkyl-aromatics, poly-aromatics, naphthenes, indanes or any combination thereof.

In an embodiment, the at least one hydrocarbon product is fractioned into gasoline, jet fuel, diesel and marine fuel boiling range or higher boiling hydrocarbons.

In an embodiment, at least 20% of the starting material is deoxygenated.

In an embodiment, at least 80% of the starting material is deoxygenated.

In an embodiment, at least 90% of the starting material is deoxygenated.

In an embodiment, the deoxygenation reaction comprises at least one of a decarboxylation reaction, decarbonylation reaction and a dehydration reaction.

In an embodiment, the deoxygenation reaction is conducted in at least one batch reactor.

In an embodiment, the deoxygenation reaction is conducted in at least one fixed bed reactor.

In an embodiment, the deoxygenation reaction is conducted is more than one successive stages.

It is further provided the use of a catalyst as defined herein in a deoxygenation reaction, in the production of biofuel or in the production of hydrocarbons.

DETAILED DESCRIPTION

The present disclosure relates to solid, heterogeneous catalysts and methods for use in the production of biofuel from naturally-occurring feedstock material. The solid, heterogeneous catalysts as described herein may be used in a deoxygenation reaction, which may include decarboxylation, decarbonylation and dehydration reactions, of the oxygenated feedstock to produce hydrocarbon products, such as those that may be used as biofuel.

The term "feedstock" as used herein refers to a substance having any detectable triglyceride and/or free fatty acid and/or carboxylic acid (whether aromatic or aliphatic) content, such as animal fats, vegetable oils, used cooking oils, biomass derived bio oils and the likes. Examples of vegetable oils include, without limitation, canola oil, corn oil, soybean oil, palm oil, coconut oil, jatropha oil, camelina oil, cottonseed oil, flax seed oil, sunflower oil, tall oil and rapeseed oil. Examples of animal fats include, without limitation, beef tallow, pork lard, and the likes. Other starting materials may also be suitable, such as glycerides present in or obtained from certain types of algae and the likes. The other oxygenated materials may also be used as starting materials such as ketone and/or alcohols.

The term "heterogeneous" as used herein with respect to solid catalysts refers to any solid physical form of suitable catalyst, whether a catalyst is calcined or otherwise hardened, whether provided in powder, pellet, balled, extruded form or anchored to a solid structure such as a metal surface, molecular sieve of natural or synthetic solid-state composition. Such catalysts are generally not solubilized during the reaction and the majority of the catalyst is recoverable from the reaction products by simple filtration.

In one embodiment, the catalyst comprises at least one metal oxide with the following general formula:

$$Al_a Cu_b Ni_c Si_d Ti_e Zn_f Zr_g La_h Ce_i W_j Sn_k Ga_l Fe_m Mo_n Mn_o Co_p O_x \quad (A)$$

wherein a, b, c, d, e, f, g, h, i, j, k, l, m, n, o, p and x are the molar ratios for the respective elements, wherein a, b, c, d, h, i, j, k, l, m, n, o and p are ≥0, e, f and g are >0 and x is such that the catalyst comprising the at least one metal oxide is electrically neutral. that is the catalyst comprising the at least one metal oxide of formula (A) comprises at least oxides of Zr, Ti and Zn and may contain one or more of Al, Cu, Ni, Si, La, Ce, W, Sn, Ga, Fe, Mo, Mn and Co. The at least one metal oxide may be from Group IIIA, IVA, IB, IIB, IIIB, IVB, VIB, VIIB and VIIIB from the periodic table.

In this non-limiting embodiment, the molar ratios for the respective elements may be as follows:

$0 \leq a \leq 4.42$ $0 \leq b \leq 1.04$ $0 \leq c \leq 1.08$ $0 \leq d \leq 3.54$ $0.39 \leq e \leq 2.79$ $0.38 \leq f \leq 2.74$ $0.13 \leq g \leq 3.42$ $0 \leq h \leq 0.12$ $0 \leq i \leq 0.40$ $0 \leq j \leq 0.27$ $0 \leq k \leq 0.25$ $0 \leq l \leq 0.41$ $0 \leq m \leq 0.20$ $0 \leq n \leq 0.28$ $0 \leq o \leq 1.26$ $0 \leq p \leq 1.08$ $X = 10$.

Any other suitable molar ratio for the respective elements may be possible in other embodiments.

In one non-limiting example, the catalyst comprising the at least one metal oxide of formula (A) is such that: b>0, c>0, e>0, f>0 and g>0, that is the catalyst comprising the at least one metal oxide of formula (A) comprises at least oxides of Zr, Ti, Zn, Ni and Cu and may contain one or more oxides of Al, Si, La, Ce, W, Sn, Ga, Fe, Mo, Mn and Co. Any other suitable (multi)metal oxide is encompassed herein. It is appreciated that the composition of the metal oxide impacts the overall efficiency (i.e., conversion efficiency of the deoxygenation reaction), performance and lifetime of the catalyst comprising the at least one metal oxide, as further discussed below. Non-limiting examples of catalysts comprising the at least one metal oxide of formula (A) are provided in Table 1.

In another embodiment, the catalyst comprises at least one metal oxide of formula (A) wherein a, b, c, d, e, f, g, h, i, j, k, l, m, n, o, p and x are the molar ratios for the respective elements, wherein a, b, c, d, e, h, i, j, k, l, m, n, o and p are ≥0, 0.38≤f≤2.74, 0.13≤g≤3.42 and x is such that the catalyst comprising the at least one metal oxide is electrically neutral. The at least one metal oxide may be from Group IIIA, IVA, IB, IIB, IIIB, IVB, VIB, VIIB and VIIIB from the periodic table.

In this non-limiting embodiment, the molar ratios for the respective elements may be as follows:

$0 \leq a \leq 4.42$ $0 \leq b \leq 1.04$ $0 \leq c \leq 1.08$ $0 \leq d \leq 3.54$ $0 \leq e \leq 2.79$ $0 \leq h \leq 0.12$ $0 \leq i \leq 0.40$ $0 \leq j \leq 0.27$ $0 \leq k \leq 0.25$ $0 \leq l \leq 0.41$ $0 \leq m \leq 0.20$ $0 \leq n \leq 0.28$ $0 \leq o \leq 1.26$ $0 \leq p \leq 1.08$ $X = 10$ Any other suitable molar ratio for the respective elements may be possible in other embodiments.

TABLE 1

Examples of catalysts comprising the at least one metal oxide of formula (A) wherein either a, b, c, d, h, i, j, k, l, m, n, o and p are ≥ 0, e, f, and g are > 0 (catalysts 2-11, 13-30) or a, b, c, d, e, h, i, j, k, l, m, n, o and p are ≥ 0, 0.38 ≤ f ≤ 2.74, 0.13 ≤ g ≤ 3.42 (catalyst 1) and x is such that the catalyst comprising the at least one metal oxide is electronically neutral.

| Catalyst Number | Composition |
|---|---|
| 1. | $Cu_{0.45}Ni_{0.34}Zn_{0.45}Zr_{4.38}O_{10}$ |
| 2. | $Ti_{1.25}Zn_{1.23}Zr_{2.67}La_{0.12}Ce_{0.38}O_{10}$ |
| 3. | $Ti_{1.85}Zn_{1.82}Zr_{1.88}La_{0.09}Ce_{0.29}O_{10}$ |
| 4. | $Ti_{2.39}Zn_{2.34}Zr_{1.21}La_{0.06}Ce_{0.19}O_{10}$ |
| 5. | $Ti_{2.79}Zn_{2.74}Zr_{0.71}La_{0.03}Ce_{0.11}O_{10}$ |
| 6. | $Al_{1.81}Ti_{1.15}Zn_{1.13}Zr_{1.64}La_{0.07}Ce_{0.23}O_{10}$ |
| 7. | $Ti_{1.27}Zn_{1.24}Zr_{2.71}W_{0.27}O_{10}$ |
| 8. | $Al_{0.11}Si_{3.54}Ti_{0.84}Zn_{0.82}Zr_{0.13}O_{10}$ |
| 9. | $Al_{0.09}Si_{2.85}Ti_{0.45}Zn_{0.44}Zr_{1.23}W_{0.12}O_{10}$ |
| 10. | $Ti_{1.05}Zn_{1.05}Zr_{3.42}O_{10}$ |
| 11. | $Al_{0.07}Si_{2.15}Ti_{1.20}Zn_{1.17}Zr_{0.86}La_{0.02}Ce_{0.13}O_{10}$ |
| 12. | $ZrO_2$ (PRIOR ART) |
| 13. | $Ti_{1.23}Zn_{1.21}Zr_{2.75}Ce_{0.40}O_{10}$ |
| 14. | $Ti_{1.22}Zn_{1.19}Zr_{2.60}La_{0.11}Ce_{0.37}Sn_{0.25}O_{10}$ |
| 15. | $Al_{4.42}Ti_{0.43}Zn_{0.42}Zr_{0.91}W_{0.09}Sn_{0.09}O_{10}$ |
| 16. | $Ti_{1.24}Zn_{1.22}Zr_{2.65}La_{0.06}Ce_{0.20}W_{0.13}Sn_{0.13}O_{10}$ |
| 17. | $Al_{0.07}Si_{3.36}Ti_{0.39}Zn_{0.38}Zr_{0.83}W_{0.08}Sn_{0.09}O_{10}$ |
| 18. | $Ti_{1.17}Zn_{1.15}Zr_{2.50}La_{0.11}Ce_{0.36}Ga_{0.41}O_{10}$ |
| 19. | $Al_{4.30}Ti_{0.42}Zn_{0.41}Zr_{0.90}W_{0.09}Ga_{0.16}O_{10}$ |
| 20. | $Ti_{1.22}Zn_{1.19}Zr_{2.60}La_{0.06}Ce_{0.19}W_{0.12}Ga_{0.22}O_{10}$ |
| 21. | $Al_{0.07}Si_{3.31}Ti_{0.39}Zn_{0.38}Zr_{0.83}W_{0.08}Ga_{0.15}O_{10}$ |
| 22. | $Ni_{0.25}Ti_{1.18}Zn_{1.16}Zr_{2.52}La_{0.11}Ce_{0.36}Ga_{0.21}O_{10}$ |
| 23. | $Al_{4.32}Ni_{0.09}Ti_{0.42}Zn_{0.41}Zr_{0.90}W_{0.09}Ga_{0.08}O_{10}$ |
| 24. | $Ni_{0.13}Ti_{1.22}Zn_{1.20}Zr_{2.61}La_{0.06}Ce_{0.19}W_{0.12}Ga_{0.11}O_{10}$ |
| 25. | $Al_{4.28}Ni_{0.09}Ti_{0.42}Zn_{0.41}Zr_{0.90}W_{0.09}Mo_{0.06}O_{10}$ |
| 26. | $Al_{4.25}Ti_{0.42}Zn_{0.41}Zr_{0.90}W_{0.09}Mo_{0.11}O_{10}$ |
| 27. | $Ti_{1.20}Zn_{1.17}Zr_{2.56}La_{0.06}Ce_{0.19}W_{0.12}Mo_{0.16}O_{10}$ |
| 28. | $Al_{4.27}Ti_{0.42}Zn_{0.41}Zr_{0.89}W_{0.09}Fe_{0.20}O_{10}$ |
| 29. | $Al_{3.65}Ni_{0.22}Ti_{0.44}Zn_{0.43}Zr_{0.93}W_{0.09}Mo_{0.28}O_{10}$ |
| 30. | $Cu_{1.04}Ni_{1.08}Ti_{0.99}Zn_{0.97}Zr_{2.10}La_{0.09}Ce_{0.30}O_{10}$ |
| 31. | $Mn_{1.26}Ti_{0.94}Zn_{0.92}Zr_{2.00}La_{0.09}Ce_{0.29}O_{10}$ |
| 32. | $Mn_{0.49}Ti_{1.09}Zn_{1.07}Zr_{2.46}La_{0.11}Ce_{0.35}O_{10}$ |
| 33. | $Cu_{0.44}Ni_{0.48}Ti_{1.15}Zn_{1.12}Zr_{2.46}W_{0.24}O_{10}$ |
| 34. | $Cu_{0.98}Ni_{1.06}Ti_{1.01}Zn_{0.99}Zr_{2.16}W_{0.21}O_{10}$ |
| 35. | $Cu_{0.48}Ni_{0.52}Ti_{1.25}Zn_{1.23}Zr_{2.67}La_{0.12}Ce_{0.38}O_{10}$ |
| 36. | $Cu_{0.53}Co_{1.07}Ti_{0.98}Zn_{0.96}Zr_{2.10}La_{0.09}Ce_{0.30}O_{10}$ |
| 37. | $Cu_{0.54}Co_{1.08}Ti_{0.99}Zn_{0.97}Zr_{2.13}W_{0.21}O_{10}$ |

In an embodiment, the catalyst comprising at least one metal oxide of formula (A) has an average surface area of for example between about 10 m²/g and about 500 m²/g and an average pore volume of for example between about 0.01 mL/g and about 1 mL/g. It is appreciated that the catalyst may also exhibit any other suitable average surface area and/or average pore volume in other embodiments.

In an embodiment, given that the solid, heterogenous catalyst is used in a deoxygenation reaction in the absence of added hydrogen (as opposed to conventional hydrogenation reactions such as hydrocracking or hydrotreating reactions that are conducted in the presence of hydrogen), the solid, heterogenous catalyst may be substantially free of noble elements that are known to act as catalysts for a hydrogenation reaction. In a non-limiting example, the solid, heterogeneous catalyst comprising at least one metal oxide of formula (A) may be substantially free of Pd, Pt, Ru, Ir and Rh since these elements are known to act as hydrotreating/hydrocracking catalysts. "Substantially free" as used herein means that the solid, heterogeneous catalyst may still comprise some impurities and/or negligible quantities of the elements known to act as catalysts for a hydrogenation reaction, however these will not have a measurably significant effect on the deoxygenation reaction. It is appreciated that these noble elements are expensive, may be easily poisoned by carbon monoxide and/or sulfur and may cause deactivation of the catalyst via carbon deposition on the catalyst surface. In other non-limiting examples, specific quantities of either one of Pd, Pt, Ru, Ir, Rh or any combination may be present in the heterogeneous catalyst comprising the at least one metal oxide of formula (A) to modify the product composition or catalyst performance.

In an embodiment, the solid, heterogeneous catalyst comprising the at least one metal oxide of formula (A) may be prepared using a variety of known methods, including but not limited to impregnation, ion-exchange, co-precipitation and/or physical mixing. While several methods are discussed below, it is appreciated that other suitable methods may be readily apparent to those skilled in the art to obtain the desired composition, shape, surface area and total pore volume of the solid, heterogeneous catalyst.

In an example, the catalyst comprising the at least one metal oxide of formula (A) may be prepared/obtained from any suitable source of its relevant elemental constituents (i.e., the relevant metal(s)) in presence or in absence of a structure directing agent. Suitable sources of the elemental constituents of the at least one metal oxide composition may be compounds such as halides, nitrates, formates, oxalates, citrates, acetates, carbonates, amine complexes, ammonium salts and/or hydroxides and hydrates of the above-mentioned metals (from Group IIIA, IVA, IB, IIB, IIIB, IVB, VIB, VIIB and VIIIB from the periodic table). A structure directing agent as used herein refers to any structural template that may be used for synthesizing structured materials, such as but not limited to a zeolite with a desired micro, meso or macro pore size.

In another example, the catalyst composition prepared/obtained from the relevant source of elemental constituents may be calcined before and/or after particle aggregation with or without concomitant use of a shaping aid, via an extruding or a pelletizing process, at a temperature between about 200° C. and about 1000° C., preferably at a temperature between about 300° C. and about 900° C., and more preferably at a temperature between about 450° C. and about 750° C. The calcination may be carried out either in the presence of an inert gas, under an oxidizing atmosphere such as air (or another suitable mixture of inert gas and molecular oxygen), under a reducing atmosphere (e.g., a mixture of inert gas, $NH_3$, CO, and/or $H_2$) or under a reduced pressure. The calcination time may be between about 30 mins and about 10 hours, preferably between about 1 hour and about 8 hours, and more preferably between about 2 and about 6 hours, the calcination time generally decreasing with increasing calcination temperature. The calcination time may be further reduced by using certain types of calcination furnaces or by selecting a suitable temperature ramping program. Catalysts calcined in the conditions described above have an average pore volume between about 0.01 mL/g and about 1.0 mL/g and an average surface area between about 10 m²/g and about 500 m²/g.

When a structure directing agent is used, the structure directing agent decomposes during calcination and may include stearic acid, malonic acid, free fatty acids derived from natural oils (vegetable oils and animal fats) or synthetic carboxylic acids and ammonium salts of the above-mentioned acids, as well as compounds such as $NH_4OH$, $(NH_4)_2CO_3$, $NH_4NO_3$, $HCOONH_4$, $CH_3COOH$, $CH_3CO_2NH_4$ and ammonium oxalate. Any other suitable structure directing agent may be used in other embodiments. Binding and/or shaping aids such as starches (e.g. potato starch and maize starch), cellulose, cellulose derivatives, microcrystalline or nanocrystalline cellulose ground nut shells and finely divided ground plastic (e.g. polyethylene, polypropylene, etc.) etc., which decompose during calcination, and or clays etc., may also be additionally incorporated.

Deoxygenation reactions catalyzed by the catalyst comprising the at least one metal oxide of formula (A) may be conducted on the following substrates: esters of fatty acids according to equation (1) below; triglycerides according to equation (2) below; or fatty acids according to equation (3) below. Such deoxygenation reactions produce hydrocarbon products from the any one of the above substrates. In one non-limiting example, the catalyst comprising the at least one metal oxide of formula (A) catalyzes a deoxygenation reaction (via decarboxylation, decarbonylation, or dehydration) of oxygenated feed oils to produce hydrocarbons according to equation (2). It is appreciated that any suitable combination of distinct catalyst comprising the at least one metal oxide of formula (A) may be used in some embodiments. Although fatty acid methyl esters and free fatty acids (or their combinations) are used in the Examples provided below, the substrate for the deoxygenation reaction may consist of various combinations containing mono, di and triglycerides, with or without corresponding methyl esters and free fatty acids.

In this embodiment, in equations (1), (2) and (3) above, R, R', R" and R'" may be the same or different, and any one of R, R', R" and R'" may be a C1 to C22 linear, branched, saturated or unsaturated chain alkyl group, which may be further substituted with hydroxyl, alkoxy or halogens like chloro, bromo or fluoro or an aryl group that can be substituted with chloro, bromo, fluoro, nitro, lower alkoxy or lower alkyl such as methyl, ethyl, propyl, isopropyl or butyl which may be further substituted with halogens such as chloro, bromo fluoro or a phenyl group that can be substituted with chloro, bromo fluoro nitro, lower alkyl or alkoxy group. Any one of R, R', R" and R'" may also be an alkyl group of a monocarboxylic acid such as acetic, propionic, butyric, caproic, caprilic, capric, lauric, myristic, palmitic, oleic, stearic or a dicarboxylic acid such as adipic acid, which are in an ester form with a C1 to C22 monohydric aliphatic alcohol such as methyl, ethyl, propyl, isopropyl, butyl and stearyl alcohol, a monohydric aromatic alcohol such as benzyl or substituted benzyl alcohol or a dihydric alcohol such as ethylene glycol, propylene glycol, butane diol or a polyhydric alcohol such as glycerol, sorbitol, polyerythritol, polyethylene glycol and poly propylene glycol and the likes. R, R', R" and R'" may be any other suitable group in other embodiments. The hydrocarbon produced in any one of equations (1), (2) or (3) may be any $C_1$-$C_{60}$ hydrocarbon or any combination thereof. The hydrocarbon produced may straight, branched, cyclic chains and/or aromatic, substituted aromatic compounds and is suitable for use as fuel and fuel applications as well as for other non-fuel applications or as a fuel blend stock.

The substrates described in equations (1), (2) and (3) above, that is esters of fatty acids, triglycerides and fatty acids, respectively, may be provided in the form of oxygenated feedstocks that will be subjected to the deoxygenation reaction with the catalyst comprising the at least one metal oxide. Oxygenated feedstocks, as used therein, therefore comprise esters of free fatty acids, triglycerides, diglycerides, monoglycerides, free fatty acids, carboxylic acids, tall oils, or any combination thereof, that may be obtained from natural resources such as, but not limited to, animal fats, vegetable oils, used cooking oils and the likes. It is appreciated that the oxygenated feedstocks that will be subjected to the deoxygenation reaction with the catalyst comprising the at least one metal oxide may not be pure and may include other compounds and impurities, such as other non-fatty acid derivatives or components/molecules, or hydrocarbons that will not react according to any one of equations (1), (2) or (3) and will not negatively impact the deoxygenation reaction. In some non-limiting embodiments, the oxygenated feedstock may be diluted with a diluent such as, but not limited to, a hydrocarbon and/or water and/or an alcohol such as methanol and/or a hydrogen donor (used in the transfer hydrogenation reaction) prior to being contacted with the catalyst comprising the at least one metal oxide for the deoxygenation reaction. Any other suitable diluent may be used in other embodiments, as encompassed herein, and it is appreciated that the diluents may impact the properties of the hydrocarbon product resulting from the deoxygenation reaction according to either one of equations (1), (2) or (3).

In one embodiment, the feedstock comprises between about 0.1 wt % and about 99.9 wt % fatty acid ester, based on the total weight of the feedstock. In another embodiment, the feedstock comprises between about 2 wt % and about 80 wt % fatty acid esters, and in still a further embodiment between about 5 wt % and about 30 wt % fatty acid esters.

In embodiments in which the feedstock is diluted with a diluent, the diluent, such as but not limited to methanol or a hydrocarbon compound, may represent between about 0.1 wt % and about 99.9 wt % of the feedstock. In other embodiments, the feedstock may comprise between about 10 wt % and about 98 wt % of the diluent, and in still other embodiments between about 50 wt % and about 95 wt % of the diluent. The feedstock, along with a hydrogen transfer agent, such as methanol, may be subjected to a pretreatment by passing through one or more catalyst (comprising the at least one metal oxide of formula (A)) or other commercial catalyst to reduce the level of unsaturation prior to the deoxygenation step. It is appreciated that other elements, including external hydrogen, may be further added to enhance or alter the composition and properties of the hydrocarbon produced, as further discussed below and encompassed herein.

In an embodiment, the feedstock is contacted with the catalyst comprising the at least one metal oxide of formula (A) within a reaction zone under conditions sufficient for converting at least a portion of the feedstock into hydrocarbon. As described previously, the deoxygenation reaction may comprise one or more distinct types of reactions that occur in the absence of added hydrogen such as, but not limited to, decarboxylation, decarbonylation, reduction, ketonization and/or dehydration, cyclization, aromatization, fragmentation and oligomerization, rather than traditional hydrogen-aided hydrotreating or hydrocracking type reactions. Specifically, the deoxygenation reaction may be conducted in a batch reactor or continuous reactor such as a fixed bed or a fluidized bed reactor. The reaction may be conducted in one, two or more successive stages. The successive stages may be identical, that is each stage has identical process parameters and uses the same catalyst comprising the at least one metal oxide of formula (A) (composition and properties), or the successive stages may be different, that is at least one of the process parameters or catalyst (composition and properties) are different. When different catalysts are used, not all catalysts may be the catalyst comprising the at least one metal oxide of formula (A), but any other suitable catalyst (i.e., conventional hydrogenation and/or isomerization catalyst or any suitable combination thereof) may be used in combination with the catalyst comprising the at least one metal oxide of formula (A).

It is appreciated that the composition and properties of the hydrocarbon obtained via either one of equations (1), (2) and (3) may be controlled, modified and/or optimized based on the feedstock being used in the deoxygenation reaction, the composition and properties of the catalyst comprising the at least one metal oxide of formula (A) as well as the process parameters of the deoxygenation reaction. Such process parameters include, but are not limited to, the temperature, pressure, and/or flow rate (i.e., weight hourly space velocity WHSV) of the deoxygenation reaction. The composition and properties of the hydrocarbon include, but are not limited to, the hydrocarbon content in aromatics, cycloalkanes, cycloolefins and oxygenates, the carbon chain length, isomerization, degree of saturation and the likes. It is appreciated that hydrocarbons with high degrees of unsaturation (i.e., with a high number of double bonds in the hydrocarbon chain) exhibit oxidative instability and therefore shorter shelf life of the hydrocarbon product. The degree of unsaturation may be modified or reduced by passing the hydrocarbon through another set of one or more catalyst (comprising the at least one metal oxide of formula (A)) beds set up in series. In a further embodiment, a transfer hydrogenation component, such as formic acid, methyl formate, methanol or a hydrogen donor agent, as used in a transfer hydrogenation reaction, could be co-fed in the reactor to enhance certain properties of the hydrocarbon.

In a non-limiting example, the deoxygenation reaction may be conducted at temperatures between about 250° C. and about 500° C., preferably between about 300° C. and about 450° C., and more preferably between about 350° C. and about 425° C. The deoxygenation reaction may be conducted at atmospheric pressure or higher pressure, such as up to about 5,000 psi, preferably between about 100 psi and about 5,000 psi, preferably between about 500 psi and about 3,000 psi and more preferably between about 750 psi and about 2,500 psi. Control of both the temperature and the pressure of the deoxygenation reaction will impact the hydrocarbon composition and properties. In a fixed bed reactor, the deoxygenation reaction may be conducted at a WHSV between about 0.09 hr$^{-1}$ and about 3 hr$^{-1}$. Control of the temperature, pressure and WHSV in such reactor may be used to control the hydrocarbon composition and properties as well as the process efficiency (i.e., conversion efficiency of the deoxygenation reaction) and active lifetime of the catalyst (i.e., the time period during which the catalyst is active without any appreciable loss or any observable loss of catalytic activity, defined as the time period over which the conversion efficiency does not decrease by more than 5% compared to the conversion efficiency at time t=0). The conversion efficiency of the deoxygenation reaction, for a given feed oil, is calculated according to equation (4) below:

$$\text{Conversion Efficiency} = \frac{Wt.\ \text{of the Feed Oil Injected} - Wt.\ \text{of Unreacted Feed oil}}{Wt.\ \text{of the Feed Oil Injected}} \times 100 \quad \text{Equation (5)}$$

The deoxygenation reaction may be characterized by the catalyst conversion efficiency of the deoxygenation reaction as defined in equation (5) above and the active lifetime of the catalyst (as defined above). In one non-limiting embodiment, deoxygenation of the feedstock according to any one of equation (1), (2), (3) or any combination thereof with the catalyst comprising the at least one metal oxide of formula (A) may deoxygenate the feedstock in the absence of added hydrogen such that the conversion efficiency is at least 20%, in some cases at least 30%, in some cases at least 40%, in some cases at least 50%, in some cases at least 60%, in some cases at least 70%, in some cases at least 80%, in some cases at least 90%, in some cases at least 95% and in some cases even more. As regards the active lifetime of the catalyst, in some non-limiting embodiments, the catalyst comprising the at least one metal oxide of formula (A) may have an active lifetime of at least 100 (continuous) days (i.e., the conversion efficiency of the catalyst comprising the at least one metal oxide of formula (A) does not decrease by more than 5% over the course of 100 days), in some cases at least 110 days, in some cases at least 120 days, in some cases at least 130 days and in some cases even more.

The deoxygenation reaction produces a liquid fraction containing the hydrocarbon that may be separated from gases also produced by the reaction. The liquid fraction containing the hydrocarbon may be fractionated using standard distillation system to separate hydrocarbon fractions into gasoline, jet fuel, diesel and marine fuel boiling ranges and heavier fractions, proportions of which depends on the catalyst and process conditions used. The hydrocarbon produced by the deoxygenation reaction may include: alkanes, iso-alkanes, cycloalkanes, normal olefin, iso-olefins, cyclic olefin, aromatics, alkyl-aromatics, poly-aromatics, naphthenes, indanes and any other hydrocarbons.

In an example of a fixed bed reactor as encompassed herein, the deoxygenation reaction may be conducted at a WHSV of between about 0.09 hr$^{-1}$ and about 3 hr$^{-1}$, preferably between about 0.2 hr$^{-1}$ and about 2.5 hr$^{-1}$, and more preferably between about 0.5 hr$^{-1}$ and about 2 hr$^{-1}$. Although the process requires no hydrogenation catalyst, adding (a) bed(s) of catalyst(s) at the end of the process sequence in series can help modify the composition of the product by enhancing the saturation levels, isoalkanes and/or aromatics levels in the product without requiring additional hydrogen.

As will be described in the Examples below, the catalyst comprising the at least one metal oxide of formula (A) and the process parameters may be adjusted or modified to produce desired variable composition of hydrocarbon or enhance composition or certain components of the product. Some examples of possible products include: hydrocarbon chains having a weight of between $C_1$-$C_{40}$, aromatics, alkyl aromatics, polyaromatics, paraffins, iso-paraffins, branched cyclo-paraffin, olefins, cyclo-olefins, naphthenes, saturated hydrocarbons, oxygen and aromatic content to name some.

It will be understood that there may be some overlap of terms used above, depending on the preferences of the use, such as preferring a particular type of hydrocarbon or a particular weight or boiling range of hydrocarbon. In addition to the hydrocarbon products, there may be other reaction products, such as carbon monoxide, carbon dioxide, gaseous hydrocarbons, hydrogen, water, etc.

EXAMPLES

All reagents used in the following examples were of technical grade. The ester of free fatty acid was made from triglyceride via transesterification reaction. Free fatty acids were prepared via hydrolysis of triglycerides. Zirconium hydroxide and doped zirconium hydroxide (may contain a trace amount of hafnium hydroxide) were purchased from Mel Chemicals UK. All other materials were purchased from Aldrich Chemical Co. Reactions were monitored by Fourier-Transform infrared Spectroscopy (FTIR) and gas chromatography (GC). The products were analyzed following ASTM protocols. Conversion (consumption of feed), oxygen content (remaining oxygen in the product) and aromatic content (aromatic % in the product) were calculated based on Fourier-transform infrared spectroscopy (FTIR) by using standard calibration methods. Simulated distillation ASTM D7169 and D86 was used to determine boiling range of the products. The product composition was determined by 2D GC. The oxidation stability of products was determined by Anton Paar PetroOxy oxidation stability tester following ASTM D7545 method. Iodine value of products was determined by titration following ASTM D5554 method. The deoxygenation products were fractionated into gasoline, diesel and jet fuel fractions using ASTM D2892 Method.

Example 1—Deoxygenation Catalysts Screening

To prepare a catalyst composition, the relevant mixture of metal oxides or metal oxide precursors obtained from any suitable source of elemental constituents was prepared by either one of impregnation, ion exchange, coprecipitation, physical mixing and/or a combination thereof, and was subsequently extruded, pelleted, pressed into tablets with tablet pressing machine or coated on a metal or any suitable surface with or without an added binder and then calcined at about 200° C. for 2 hours and then at about 550° C. for 4 hours in static air in a programmable furnace. The calcined tablets so obtained were then crushed and sieved between 10 and 20 mesh sizes.

Figure 1:
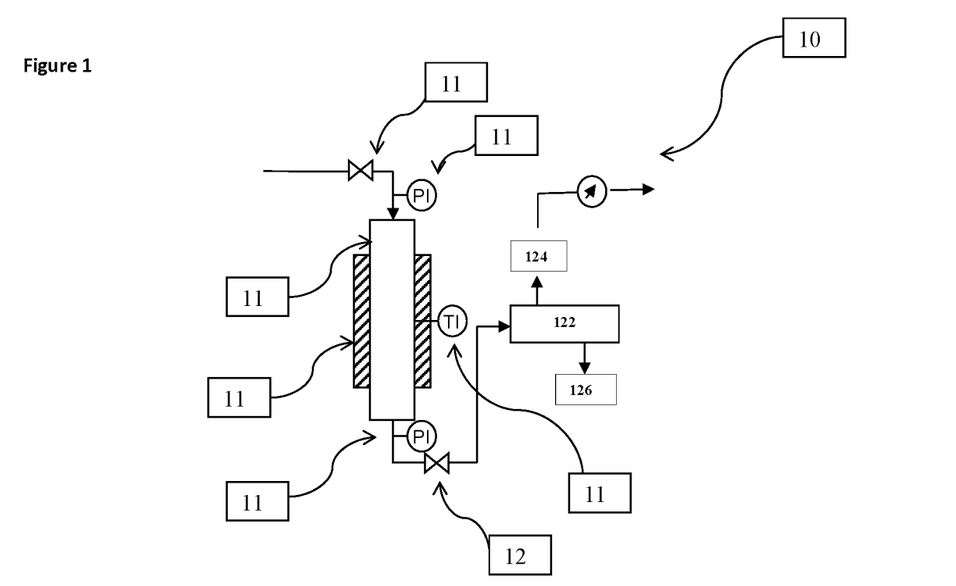
FIG. 1 shows a system for screening solid, heterogeneous catalysts in a single bed reactor in accordance with one embodiment.

With reference to FIG. 1, a system 100 for the screening of solid, heterogenous catalysts in a single bed reactor (and performing a deoxygenation reaction) is shown. Approximately 20 g of a catalyst sample is placed in a ½" tubular stainless-steel single bed reactor 110. The catalyst bed may be diluted with inert materials such as silicon carbide to fill interparticle space for better distribution of reacting materials and heat distribution to form a catalyst bed that is to be used in the deoxygenation reaction. The reactor 110 is connected to, at the inlet of the reactor 110: (1) a positive displacement metering pump 112 at the inlet of the reactor 110 for feeding in the feed oil (feedstock); and (2) a pressure gauge 114 for measuring a pressure at the inlet of the reactor 100. The reactor 100 is also connected to another pressure gauge 116 at the outlet of the reactor 100 to measure and monitor the process pressure and the pressure differential (i.e., the pressure difference between the outlet and the inlet of the reactor 110), if any, generated during operation of the reactor 110. The pressure of the reactor 110 is controlled using a variable pressure control valve. The system 100 is also equipped with an emergency safety pressure relief system and system shut off capability. The required process temperature is: (1) achieved and maintained by placing the reactor 110 in a tube muffle furnace 117; and (2) monitored by placing temperature sensors 118 inside and outside of the reactor 110.

For the purpose of the screening, a large variety of fatty acid methyl esters derived from several commercially-available vegetable oils and animal fats sources were subjected to deoxygenation reactions with solid, heterogeneous catalysts (i.e., in accordance with Equation 1 above) in several (parallel) continuous reactor systems similar to the system 100. The catalysts affect deoxygenation of above feed stocks in manners similar to canola derived feed stock.

To this end, feed oil largely consisting of canola oil-derived fatty acid methyl esters and free fatty acids, is fed into the fixed bed reactor 110 holding the catalyst preparation at a flow rate of about 0.2 ml/min. The temperature of the bed of the reactor 110 was maintained at about 415° C. and the pressure was maintained at about 950 psi. The effluents from the reactor 110 were released at atmospheric pressure, cooled using a cooling condenser and then passed through a gas liquid separator 122 to separate gaseous products 124 from liquid fractions 126 containing the hydrocarbons.

Several solid, heterogeneous catalyst compositions were screened using the system 100. Each catalyst was tested for a period of at least 3 days. The effect of various elements (i.e., the effect of the composition of the heterogeneous catalysts) on the deoxygenation of oxygenates was determined. Data relating to the conversion efficiency of a reaction of deoxygenation of feed oil largely consisting of canola oil-derived fatty acid methyl esters and free fatty acids with various catalyst compositions, as well as the oxygen and aromatic contents (in weight %) in the product stream post-deoxygenation reaction, are shown in Table 2. The oxygen and aromatic content in the product stream were determined using FTIR.

TABLE 2 conversion efficiency of a reaction of deoxygenation of feed oil largely consisting of cannola oil-derived fatty acid methyl esters and free fatty acids with various catalyst compositions, as well as oxygen and aromatic contents in the product stream.

| Sr. # | Catalyst composition | Oxygen content (wt %) | Aromatic content (wt %) | Conversion Efficiency (%) |
|---|---|---|---|---|
| 1 | $Cu_{0.45}Ni_{0.34}Zn_{0.45}Zr_{4.38}O_{10}$ | 0.72 | 11.87 | 99.43 |
| 2 | $Ti_{1.25}Zn_{1.23}Zr_{2.67}La_{0.12}Ce_{0.38}O_{10}$ | 0.1 | 10.10 | 100 |
| 3 | $Ti_{1.85}Zn_{1.82}Zr_{1.88}La_{0.09}Ce_{0.29}O_{10}$ | 0.4 | 5.58 | 98.97 |
| 4 | $Ti_{2.39}Zn_{2.34}Zr_{1.21}La_{0.06}Ce_{0.19}O_{10}$ | 0.37 | 4.66 | 99.06 |
| 5 | $Ti_{2.79}Zn_{2.74}Zr_{0.71}La_{0.03}Ce_{0.11}O_{10}$ | 0.37 | 4.87 | 98.94 |

TABLE 2-continued conversion efficiency of a reaction of deoxygenation of feed oil largely consisting of canola oil-derived fatty acid methyl esters and free fatty acids with various catalyst compositions, as well as oxygen and aromatic contents in the product stream.

| Sr. # | Catalyst composition | Oxygen content (wt %) | Aromatic content (wt %) | Conversion Efficiency (%) |
|---|---|---|---|---|
| 6 | $Al_{1.81}Ti_{1.15}Zn_{1.13}Zr_{1.64}La_{0.07}Ce_{0.23}O_{10}$ | 0.38 | 3.24 | 98.52 |
| 7 | $Ti_{1.27}Zn_{1.24}Zr_{2.71}W_{0.27}O_{10}$ | 0 | 21.27 | 100.00 |
| 8 | $Al_{0.11}Si_{3.54}Ti_{0.84}Zn_{0.82}Zr_{0.13}O_{10}$ | 0.1 | 19.99 | 99.86 |
| 9 | $Al_{0.09}Si_{2.85}Ti_{0.45}Zn_{0.44}Zr_{1.23}W_{0.12}O_{10}$ | 0.05 | 19.61 | 100.00 |
| 10 | $Ti_{1.05}Zn_{1.05}Zr_{3.42}O_{10}$ | 0.8 | 5.76 | 98.68 |
| 11 | $Al_{0.07}Si_{2.15}Ti_{1.20}Zn_{1.17}Zr_{0.86}La_{0.02}Ce_{0.13}O_{10}$ | 0.12 | 32.05 | 98.57 |
| 12 | $ZrO_2$ (PRIOR ART) | 0.99 | 3.04 | 97.53 |
| 13 | $Ti_{1.23}Zn_{1.21}Zr_{2.75}Ce_{0.40}O_{10}$ | 0.82 | 2.4 | 98.12 |

As shown in Table 2, the conversion efficiency was at least 98% for all catalyst compositions tested. By selecting a suitable catalyst composition, the oxygen and the aromatic content in the product stream can be controlled and therefore the product stream may be used for specific applications (i.e., aviation fuel with 0% oxygen, etc.) or in specific jurisdictions with specific requirements in terms of oxygen or aromatic content. For the catalyst compositions tested, the oxygen content in the product stream varies between 0 and 0.99% while the aromatic content in the product stream varies between 2.4% and 32%. Use of the catalyst compositions with Al, Si and W (e.g., catalysts 7, 8, 9 and 11) results in a high content of aromatics in the product stream (i.e., at least 19 wt %), which can notably improve the cold properties of the product stream. It was also found that use of catalyst compositions with Ti, Zn, La and Ce has no significant impact on the aromatic and or oxygen contents of the product, however contribute to an increase of the active lifetime of the catalyst. A high content of Zr, Ti and Zn effectively deoxygenates and suppresses coke formation while the presence of and $La_2O_3$ and $CeO_2$ is known to maintain the crystalline structure of $ZrO_2$, thereby, extending the active lifetime of the catalyst (Applied Catalysis, 78 (1991) 79-96). As a non-limiting example, catalyst 12 ($ZrO_2$) exhibits an active lifetime of 3 days. When compared with a catalyst further comprising ZnO and $TiO_2$, such as catalyst 10 ($Ti_{1.05}Zn_{1.05}Zr_{3.42}O_{10}$), the active lifetime of the catalyst is extended to 10 days. When further compared with a catalyst further comprising La and Ce, such as catalyst 2 ($Ti_{1.25}Zn_{1.23}Zr_{2.67}La_{0.12}Ce_{0.38}O_{10}$), the active lifetime was increased to more than 100 days.

Example 2—Representative Examples of Catalyst Preparation

Catalyst 2 from Table 2 was prepared by doping a mixture of zirconium hydroxide with $La_2O_3$ and $CeO_2$ (100 g), zinc oxide (20 g) and titanium oxide (20 g) and then pressing the resulting mixture into tablets with a tablet pressing machine and then calcining the tablets at 200° C. for 2 hours and then at 550° C. for 4 hours in static air in a programmable furnace. The calcined tablets were then crushed and sieved between 10 and 20 mesh sizes. The catalyst composition so obtained has a surface area of about 78.33 $m^2/g$ and a total pore volume of about 0.61 mL/g. Similarly, Catalyst 7 from Table 2 was prepared by doping a mixture of zirconium hydroxide with tungsten trioxide (100 g), zinc oxide (20 g) and titanium oxide (20 g) and then pressing the resulting mixture into tablets with a tablet pressing machine and then calcining the tablets at 200° C. for 2 hours and then at 550° C. for 4 hours in static air in a programmable furnace. The calcined tablets were crushed and sieved between 10 and 20 mesh sizes. The catalyst composition so obtained has a surface area of about 76 $m^2/g$ and a total pore volume of about 0.46 mL/g.

Example 3—Process Conditions

With reference to FIG. 1, the process conditions including (reactor 110 inlet and reactor 110 outlet) pressure, temperature, flow rate (specifically, weight hourly space velocity WHSV) as well as methanol diluent and water diluent were evaluated by using catalyst composition 2 from Table 2 as catalyst and canola biodiesel (canola fatty acid methyl ester) as the feedstock in the system 100.

Figure 2:
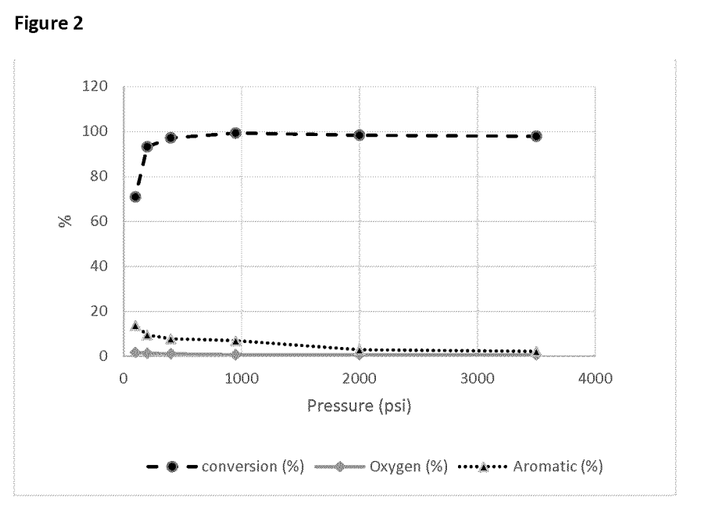
FIG. 2 shows a plot of pressure vs. conversion efficiency, content of oxygen and content of aromatic in the product stream for a deoxygenation reaction of canola biodiesel (canola fatty acid methyl ester) in the system of FIG. 1, in accordance with one embodiment.

The pressure variation effect between the inlet and the outlet of the reactor 110 was assessed by keeping the WHSV constant at about 0.56 $h^{-1}$ and by keeping a constant temperature of about 415° C. The results are shown in table 3 and in FIG. 2. Table 3 and FIG. 2 demonstrate that while lower pressures tend to generate higher aromatic contents, pressures over about 200 psi increase the conversion efficiency and reduce the overall oxygen content in the product stream.

TABLE 3

Conversion efficiency, oxygen and aromatic contents in the product stream for various pressures.

| Pressure (psi) | WHSV ($h^{-1}$) | Temperature (° C.) | Conversion Efficiency (%) | Oxygen Content (%) | Aromatic Content (%) |
|---|---|---|---|---|---|
| 3500 | 0.56 | 415 | 97.74 | 0.55 | 2.1 |
| 2000 | 0.56 | 415 | 98.19 | 0.59 | 2.79 |
| 950 | 0.56 | 415 | 99.18 | 0.59 | 6.85 |

TABLE 3-continued

Conversion efficiency, oxygen and aromatic contents
in the product stream for various pressures.

| Pressure (psi) | WHSV ($h^{-1}$) | Temperature (° C.) | Conversion Efficiency (%) | Oxygen Content (%) | Aromatic Content (%) |
| --- | --- | --- | --- | --- | --- |
| 400 | 0.56 | 415 | 96.96 | 1.01 | 7.68 |
| 200 | 0.56 | 415 | 93.08 | 1.24 | 9.42 |
| 100 | 0.56 | 415 | 70.76 | 1.58 | 13.74 |

Figure 3:
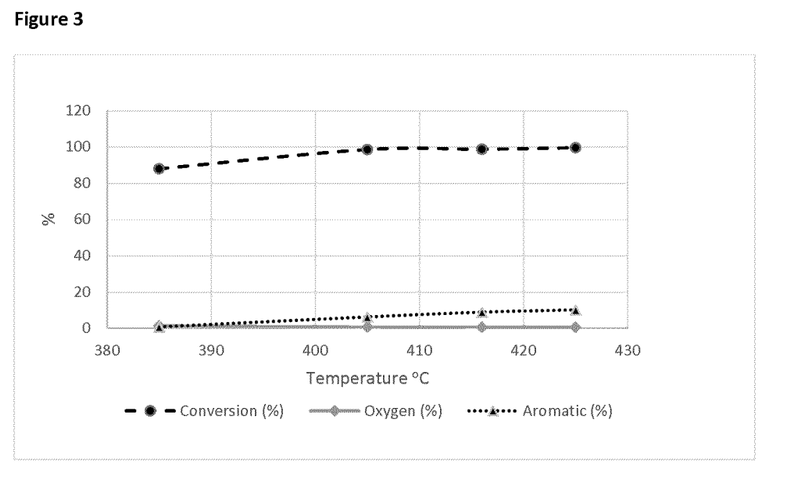
FIG. 3 shows a plot of temperature vs. conversion efficiency, content of oxygen and content of aromatic in the product stream for a deoxygenation reaction of canola biodiesel (canola fatty acid methyl ester) in the system of FIG. 1, in accordance with one embodiment.

The impact of the process temperature was further evaluated by keeping the WHSV constant at about 0.56 $h^{-1}$ and the pressure constant at about 950 psi while changing the process temperature. The results are presented in Table 4 and FIG. 3 and show that the conversion efficiency, oxygen and aromatic contents in the product stream increase with increasing process temperatures.

TABLE 4

Conversion efficiency, oxygen and aromatic contents
in the product stream for various temperatures.

| Temperature (° C.) | Pressure (psi) | WHSV ($h^{-1}$) | Conversion Efficiency (%) | Oxygen Content (%) | Aromatic Content (%) |
| --- | --- | --- | --- | --- | --- |
| 385 | 950 | 0.56 | 87.84 | 1.26 | 0.64 |
| 405 | 950 | 0.56 | 98.41 | 0.61 | 6.14 |
| 416 | 950 | 0.56 | 98.58 | 0.58 | 8.79 |
| 425 | 950 | 0.56 | 99.39 | 0.48 | 10.05 |

Figure 4:
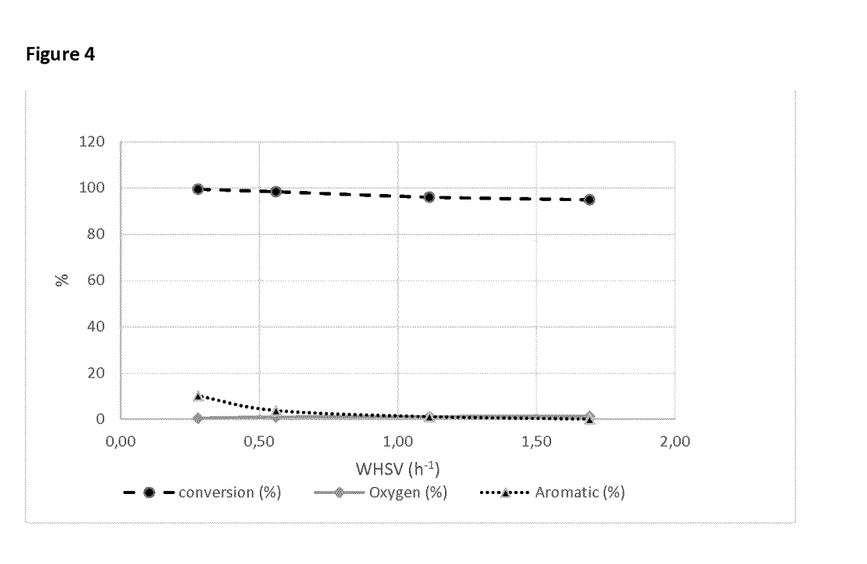
FIG. 4 shows a plot of weight hour space velocity (WHSV) vs. conversion efficiency, content of oxygen and content of aromatic in the product stream for a deoxygenation reaction of canola biodiesel (canola fatty acid methyl ester) in the system of FIG. 1, in accordance with one embodiment.

The impact of the WHSV was further evaluated by keeping the pressure at about 400 psi and the process temperature at about 415° C. while changing the WHSV. The results are shown in Table 5 and FIG. 4 and show that reducing the WHSV from about 1.69 $h^{-1}$ to about 0.28 $h^{-1}$ increases the conversion efficiency, decreases the oxygen content and increases the aromatic content.

TABLE 5

Conversion efficiency, oxygen and aromatic contents
in the product stream for various WHSV.

| WHSV ($h^{-1}$) | Pressure (psi) | Temperature (° C.) | Conversion Efficiency (%) | Oxygen Content (%) | Aromatic Content (%) |
| --- | --- | --- | --- | --- | --- |
| 1.69 | 400 | 415 | 94.76 | 1.2 | 0 |
| 1.11 | 400 | 415 | 95.89 | 1.13 | 1.01 |
| 0.56 | 400 | 415 | 98.24 | 0.89 | 3.69 |
| 0.28 | 400 | 415 | 99.31 | 0.42 | 10.04 |

Figure 5:
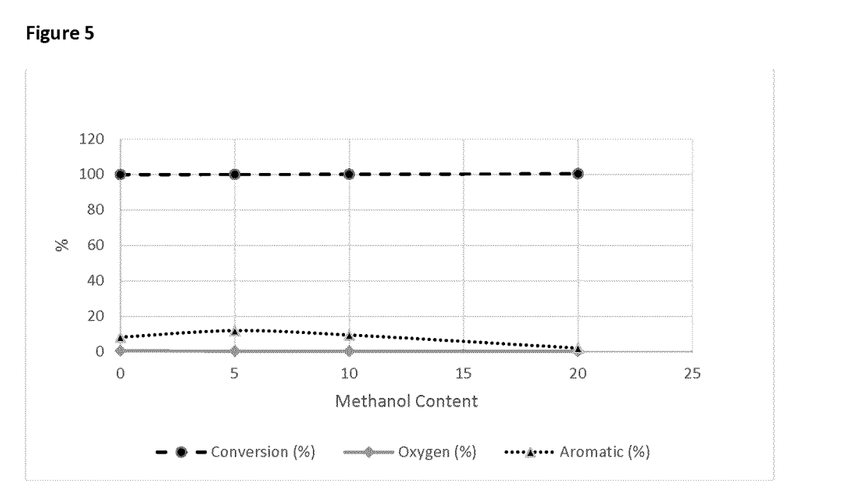
FIG. 5 shows a plot of methanol content vs. conversion efficiency, content of oxygen and content of aromatic in the product stream for a deoxygenation reaction of canola biodiesel (canola fatty acid methyl ester) in the system of FIG. 1, in accordance with one embodiment.

The canola biodiesel was diluted with methanol and the impact of methanol dilution was evaluated by changing the methanol concentration for the dilution while keeping the process temperature, pressure and WHSV constant. The results are shown in Table 6 and FIG. 5 and demonstrate that increasing the methanol concentration from 0% to 20% has no significant impact on the conversion efficiency (which in this case, is always >99%), however it reduces both the oxygen content from 0.38% to 0.13% and the aromatic content from 10.52% to 7.88%.

TABLE 6

Conversion efficiency, oxygen and aromatic contents
in the product stream for various methanol concentrations.

| MeOH (%) | Temperature (° C.) | Pressure (psi) | WHSV ($h^{-1}$) | Conversion Efficiency (%) | Oxygen Content (%) | Aromatic Content (%) |
| --- | --- | --- | --- | --- | --- | --- |
| 0 | 415 | 950 | 0.56 | 99.40 | 0.38 | 10.52 |
| 5 | 415 | 950 | 0.56 | 99.62 | 0.22 | 9.40 |
| 10 | 415 | 950 | 0.56 | 99.94 | 0.15 | 9.28 |
| 20 | 415 | 950 | 0.56 | 100 | 0.13 | 7.88 |

Figure 6:
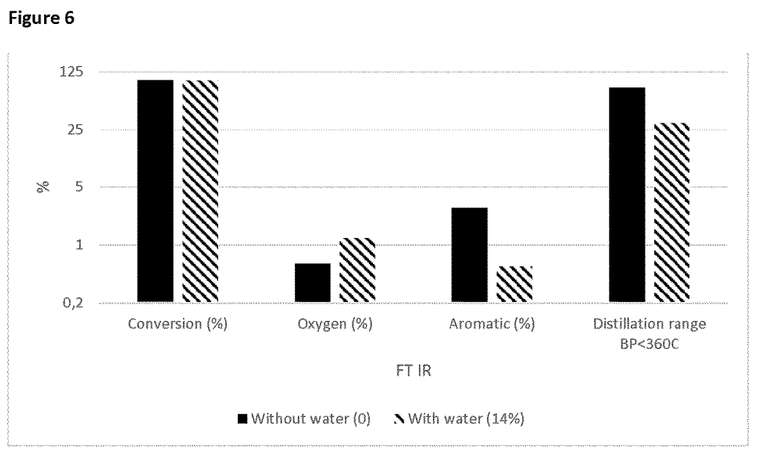
FIG. 6 shows conversion efficiency, content of oxygen and content of aromatic in the product stream as well as fraction of the product distilling in a specific distillation range for a deoxygenation reaction of canola biodiesel (canola fatty acid methyl ester) in the absence or the presence of water in the system of FIG. 1, in accordance with one embodiment.

To further study the impact of water addition/dilution, water and the canola biodiesel (feedstock) were introduced in the reactor 110 using separate pumps, keeping all other process parameters constant. The results are shown in Table 7 and FIG. 6 and demonstrate that dilution with water has a dramatic impact on both oxygen and aromatic contents in the product stream (i.e., the product properties) and the fraction of the product distilling in the distillation range <360° C. Specifically, less product distills in the temperature range <360° C. in presence of water compared to in the absence of water. It is appreciated that a product stream with a higher oxygen content exhibits a lower oxidation stability, while a product stream with a higher aromatic content exhibits improved cold properties.

TABLE 7

Conversion efficiency, oxygen and aromatic contents in the product stream and
distillation range with and without dilution with water.

| $H_2O$ in feed (%) | Temperature (° C.) | Pressure (psi) | WHSV ($h^{-1}$) | Conversion Efficiency (%) | Oxygen Content (%) | Aromatic Content (%) | Distillation Range <360° C. |
| --- | --- | --- | --- | --- | --- | --- | --- |
| 0 | 415 | 2000 | 0.56 | 98.19 | 0.59 | 2.79 | 90% |
| 14 | 415 | 2000 | 0.56 | 96.92 | 1.21 | 0.55 | 30% |

Figure 7:
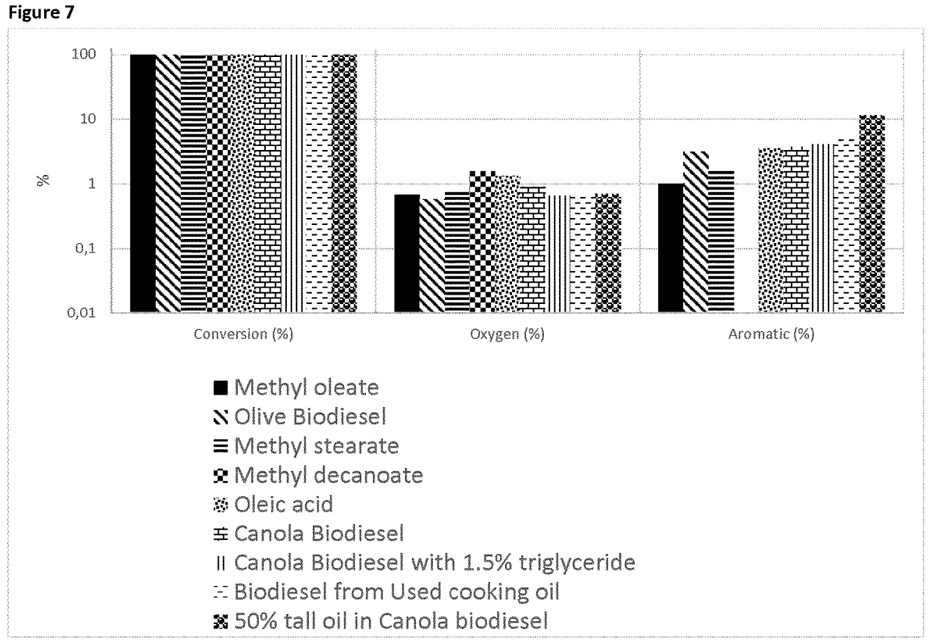
FIG. 7 show conversion efficiency, content of oxygen and content of aromatic, respectively, in the product stream for a deoxygenation reaction of various feedstock in the system of FIG. 1, in accordance with one embodiment.

A variety of feedstocks including methyl oleate, olive biodiesel, methyl stearate, methyl decanoate, oleic acid, canola biodiesel, canola biodiesel with 1.5% triglyceride, 1.3% diglycerides, 4.8% monoglycerides, biodiesel from used cooking oil and 50% tall oil in canola biodiesel were subjected to deoxygenation in presence of the catalyst composition 2 of Table 2 in the system 100. The results are shown in Table 8 and FIG. 7 which show that the conversion for all the feedstocks is similar and close to 100% conversion ranging from 96.74% to 100%. Residual oxygen content of the products from different feedstocks are also similar ranging from 0.57% to 1.54%. aromatic level of the products from different feedstocks are all below 4% ranging from 0% to 11.39%.

TABLE 8

Conversion efficiency, oxygen and aromatic contents in the product stream for various feedstock.

| Temperature (° C.) | Pressure (psi) | WHSV ($h^{-1}$) | Feed | Conversion Efficiency (%) | Oxygen Content (%) | Aromatic Content (%) |
|---|---|---|---|---|---|---|
| 415 | 400 | 0.56 | Methyl oleate | 98.27 | 0.67 | 1 |
| 415 | 400 | 0.56 | Olive Biodiesel | 98.73 | 0.57 | 3.12 |
| 415 | 400 | 0.56 | Methyl stearate | 98.8 | 0.75 | 1.63 |
| 415 | 400 | 0.28 | Methyl decanoate | 96.74 | 1.54 | 0 |
| 415 | 400 | 0.56 | Oleic acid | 98.79 | 1.3 | 3.49 |
| 415 | 400 | 0.56 | Canola Biodiesel | 98.24 | 0.89 | 3.69 |
| 415 | 950 | 0.56 | Canola Biodiesel with 1.5% triglycerides, 1.3% Diglycerides, 4.8% Monoglycerides | 98.60 | 0.64 | 3.20 |
| 415 | 950 | 0.56 | Biodiesel from Used cooking oil | 98.22 | 0.62 | 4.78 |
| 415 | 2100 | 0.66 | 50% tall oil in Canola biodiesel | 98.05 | 0.69 | 11.39 |
| 415 | 950 | 0.56 | Canola Biodiesel | 100 | 0.1 | 10.43 |

Example 4—Multiple Bed System

Figure 8:
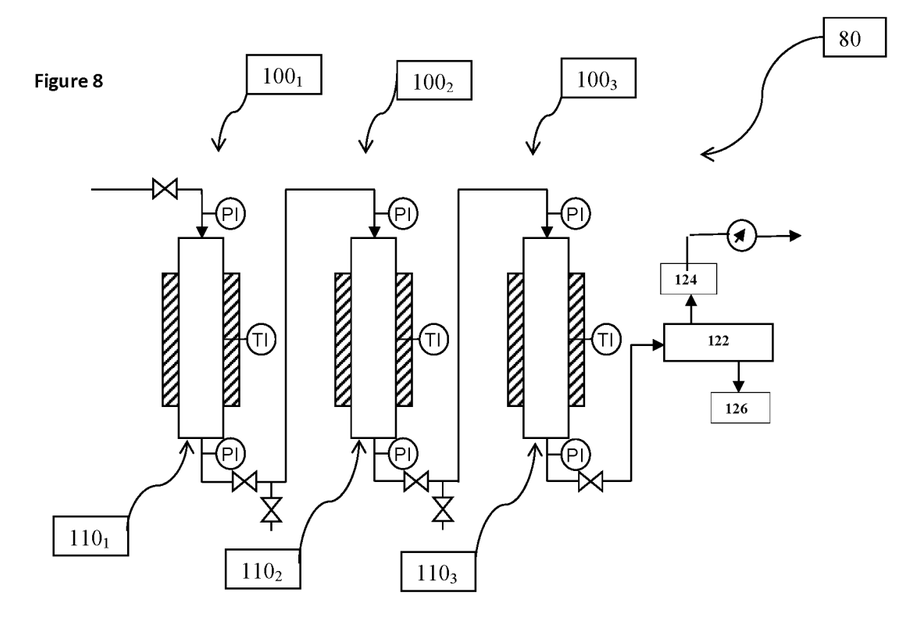
FIG. 8 shows a system for testing solid, heterogeneous catalysts in a plurality of single bed reactors in accordance with another embodiment.

With further reference to FIG. 8, another system 800 for performing a deoxygenation reaction is shown. The system 800 essentially comprises a plurality of systems 100 in series (i.e., a first system $100_1$ in which the outlet of the first reactor $110_1$ is connected to a second system $100_2$ in which the outlet of the second reactor $110_2$ is connected to a third system $100_3$).

Reaction products from the fixed bed reactor $110_1$ with a catalyst as described in Table 2 may be subjected to further processing by introducing the reaction products from the reactor bed $110_1$ into a second reactor $110_2$ and then into a third reactor $110_3$. Any other suitable configuration may be possible in other embodiments. These reactors $110_2$ and $110_3$ may comprise similar or different catalyst preparations from that of reactor $110_1$ to further enhance the content of certain desired components in the hydrocarbon product, decrease the content of undesired components or enhance saturation or isomerization or fragmentation of the resulting hydrocarbon product and/or to further increase the oxidation stability and the shelf life of the hydrocarbon product without requiring additional hydrogen.

Figure 9:
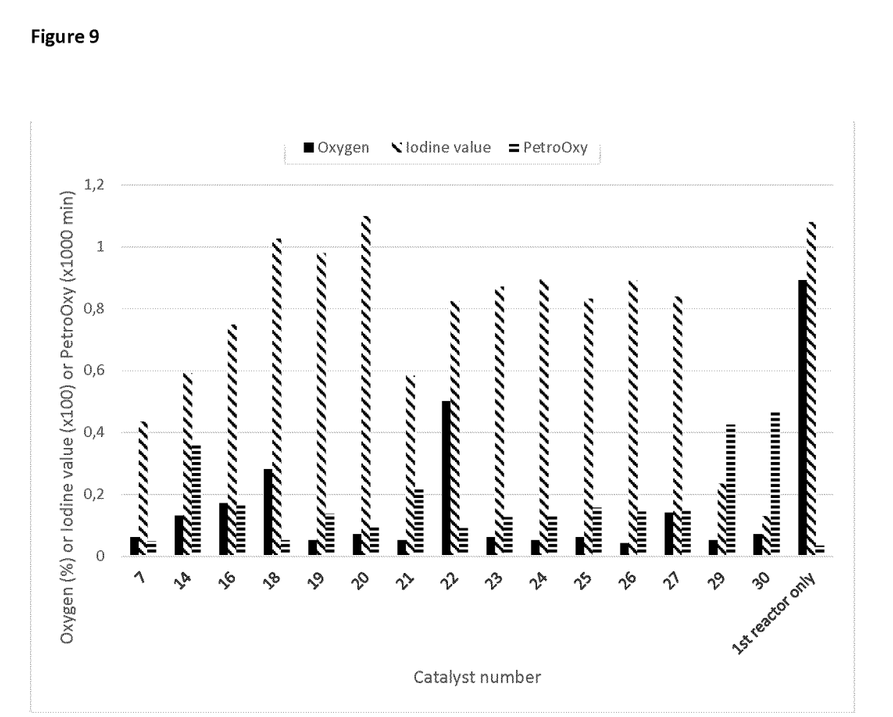
FIG. 9 show content of oxygen, iodine value (unsaturation) and oxidative stability (PetroOxy induction time), respectively, in the product stream for a deoxygenation reaction in a two-reactor system using various catalysts, in accordance with one embodiment.

Table 9 and FIG. 9 show results for a two-reactor system using various catalyst and specifically the impact of the different catalysts on the remaining oxygenate contents, unsaturation (iodine values) and oxidative stability (PetrOxy Induction Time) of the hydrocarbon product.

TABLE 9

Oxygen contents, iodine values (unsaturation) and oxidative stability (PetroOxy induction time) in the product stream for a deoxygenation reaction in a two-reactor system using various catalysts.

| Catalysts | | Oxygen content (%) | | Iodine value | | PetroOxy Induction Time (min.) | |
|---|---|---|---|---|---|---|---|
| Reactor 1 | Reactor 2 | Reactor 1 | Reactor 2 | Reactor 1 | Reactor 2 | Reactor 1 | Reactor 2 |
| 2 | 7 | 0.89 | 0.06 | 107.9 | 43.4 | 32.8 | 46.98 |
| 2 | 14 | 0.89 | 0.13 | 107.9 | 59.1 | 32.8 | 357.53 |
| 2 | 16 | 0.89 | 0.17 | 107.9 | 74.7 | 32.8 | 164.45 |
| 2 | 18 | 0.89 | 0.28 | 107.9 | 102.6 | 32.8 | 50.91 |
| 2 | 19 | 0.89 | 0.05 | 107.9 | 97.9 | 32.8 | 136.55 |
| 2 | 20 | 0.89 | 0.07 | 107.9 | 109.8 | 32.8 | 98.26 |
| 2 | 21 | 0.89 | 0.05 | 107.9 | 58.2 | 32.8 | 220.13 |
| 2 | 22 | 0.89 | 0.5 | 107.9 | 82.3 | 32.8 | 89.05 |
| 2 | 23 | 0.89 | 0.06 | 107.9 | 87 | 32.8 | 125.18 |
| 2 | 24 | 0.89 | 0.05 | 107.9 | 89.3 | 32.8 | 130.03 |
| 2 | 25 | 0.89 | 0.06 | 107.9 | 83.2 | 32.8 | 155.1 |
| 2 | 26 | 0.89 | 0.04 | 107.9 | 89 | 32.8 | 142.76 |
| 2 | 27 | 0.89 | 0.14 | 107.9 | 83.8 | 32.8 | 146.45 |

TABLE 9-continued

Oxygen contents, iodine values (unsaturation) and oxidative stability
(PetroOxy induction time) in the product stream for a deoxygenation reaction in
a two-reactor system using various catalysts.

| Catalysts | | Oxygen content (%) | | Iodine value | | PetroOxy Induction Time (min.) | |
|---|---|---|---|---|---|---|---|
| Reactor 1 | Reactor 2 | Reactor 1 | Reactor 2 | Reactor 1 | Reactor 2 | Reactor 1 | Reactor 2 |
| 2 | 29 | 0.89 | 0.05 | 107.9 | 23.3 | 32.8 | 423.85 |
| 2 | 30 | 0.89 | 0.07 | 107.9 | 12.8 | 32.8 | 469.15 |

Table 10 shows results for a three-reactor system using various catalyst and specifically the impact of the different combination of catalysts on the remaining oxygenate contents, unsaturation (iodine values) and oxidative stability (PetrOxy Induction Time) of the hydrocarbon product.

TABLE 10

Oxygen contents, iodine values (unsaturation) and oxidative stability
(PetroOxy induction time) of the hydrocarbon product in the
product stream for a deoxygenation reaction in a three-reactor
system using various catalysts.

| Catalysts | | | Oxygen (%) | Iodine value | PetroOxy Induction Time (min.) |
|---|---|---|---|---|---|
| Reactor 1 | Reacttor 2 | Reactor 3 | | | |
| 30 | 31 | 30 | 0.05 | 28.3 | 233.55 |
| 30 | 31 | 34 | 0.07 | 19.3 | 373.03 |
| 35 | 32 | 33 | 0.05 | 6.7 | 755.36 |
| 30 | 31 | 33 | 0.04 | 8.4 | 814.85 |
| 36 | 31 | 37 | 0.06 | 51.4 | 283.58 |

As encompassed herein, the word "comprising" is used in its non-limiting sense to mean that items following the word are included, but items not specifically mentioned are not excluded. A reference to an element by the indefinite article "a" does not exclude the possibility that more than one of the elements is present, unless the context clearly requires that there be one and only one of the elements.

The scope of the following claims should not be limited by the preferred embodiments set forth in the examples above and in the drawings, but should be given the broadest interpretation consistent with the description as a whole.

The invention claimed is:

1. A catalyst comprising at least three metal oxides having a formula $Al_aCu_bNi_cSi_dTi_eZn_fZr_gLa_hCe_iW_jSn_kGa_lFe_m\text{-}MO_nMn_oCO_pO_x$, wherein a, b, c, d, e, f, g, h, i, j, k, l, m n, o, p and x are molar ratios for the respective elements, wherein a, b, c, d, h, i, j, k, l, m, n, o and p are ≥0, e, f and g are >0 and x is such that the catalyst is electrically neutral, and the catalyst is substantially free of any one of Pd, Pt, Ru, Ir, and Rh.

2. The catalyst of claim 1, wherein the catalyst is one of:
$Cu_{0.45}Ni_{0.34}Zn_{0.45}Zr_{4.38}O_{10}$
$Ti_{1.25}Zn_{1.23}Zr_{2.67}La_{0.12}Ce_{0.38}O_{10}$
$Ti_{1.85}Zn_{1.82}Zr_{1.88}La_{0.09}Ce_{0.29}O_{10}$
$Ti_{2.39}Zn_{2.34}Zr_{1.21}La_{0.06}Ce_{0.19}O_{10}$
$Ti_{2.79}Zn_{2.74}Zr_{0.71}La_{0.03}Ce_{0.11}O_{10}$
$Al_{1.81}Ti_{1.15}Zn_{1.13}Zr_{1.64}La_{0.07}Ce_{0.23}O_{10}$
$Ti_{1.27}Zn_{1.24}Zr_{2.71}W_{0.27}O_{10}$
$Al_{0.11}Si_{3.54}Ti_{0.84}Zn_{0.82}Zr_{0.13}O_{10}$
$Al_{0.09}Si_{2.85}Ti_{0.45}Zn_{0.44}Zr_{1.23}W_{0.12}O_{10}$
$Ti_{1.05}Zn_{1.05}Zr_{3.42}O_{10}$
$Al_{0.07}Si_{2.15}Ti_{1.20}Zn_{1.17}Zr_{0.86}La_{0.02}Ce_{0.13}O_{10}$
$Ti_{1.23}Zn_{1.21}Zr_{2.75}Ce_{0.40}O_{10}$
$Ti_{1.22}Zn_{1.19}Zr_{2.60}La_{0.11}Ce_{0.37}Sn_{0.25}O_{10}$
$Al_{4.42}Ti_{0.43}Zn_{0.42}Zr_{0.91}WV_{0.09}Sn_{0.09}O_{10}$
$Ti_{1.24}Zn_{1.22}Zr_{2.65}La_{0.06}Ce_{0.20}W_{0.13}Sn_{0.13}O_{10}$
$Al_{0.07}Si_{3.36}Ti_{0.39}Zn_{0.38}Zr_{0.83}W_{0.82}Sn_{0.09}O_{10}$
$Ti_{1.17}Zn_{1.15}Zr_{2.50}La_{0.11}Ce_{0.36}Ga_{0.41}O_{10}$
$Al_{4.30}Ti_{0.42}Zn_{0.41}Zr_{0.90}WV_{0.09}Ga_{0.16}O_{10}$
$Ti_{1.22}Zn_{1.19}Zr_{2.60}La_{0.06}Ce_{0.19}W_{0.12}Ga_{0.22}O_{10}$
$Al_{0.07}Si_{3.31}Ti_{0.39}Zn_{0.38}Zr_{0.83}W_{0.08}Ga_{0.15}O_{10}$
$Ni_{0.25}Ti_{1.18}Zn_{1.16}Zr_{2.52}La_{0.11}Ce_{0.36}Ga_{0.21}O_{10}$
$Al_{4.32}Ni_{0.09}Ti_{0.42}Zn_{0.41}Zr_{0.90}W_{0.09}Ga_{0.08}O_{10}$
$Ni_{0.13}Ti_{1.22}Zn_{1.20}Zr_{2.61}La_{0.06}Ce_{0.19}W_{0.12}Ga_{0.11}O_{10}$
$Al_{4.28}Ni_{0.09}Ti_{0.42}Zn_{0.41}Zr_{0.90}WV_{0.09}Mo_{0.06}O_{10}$
$Al_{4.25}Ti_{0.42}Zn_{0.41}Zr_{0.90}W_{0.09}Mo_{0.11}O_{10}$
$Ti_{1.20}Zn_{1.17}Zr_{2.56}La_{0.06}Ce_{0.19}W_{0.12}Mo_{0.16}O_{10}$
$Al_{4.27}Ti_{0.42}Zn_{0.41}Zr_{0.89}WV_{0.09}Fe_{0.20}O_{10}$
$Al_{3.65}Ni_{0.22}Ti_{0.44}Zn_{0.43}Zr_{0.93}W_{0.09}Mo_{0.28}O_{10}$
$Cu_{1.04}Ni_{1.08}Ti_{0.99}Zn_{0.97}Zr_{2.10}La_{0.09}Ce_{0.30}O_{10}$.

3. The catalyst of claim 1, wherein the catalyst has a surface area between about 10 $m^2$/g and about 500 $m^2$/g.

4. The catalyst of claim 1, wherein the catalyst has a total pore volume between about 0.01 mL/g and about 1 mL/g.

5. The catalyst of claim 1, wherein the catalyst is in powdered, pelleted, extruded form or coated on a metal or any suitable surface with or without an added binder.

6. The catalyst of claim 1, wherein the catalyst is calcined.

7. A method for performing a deoxygenation reaction of a starting material, comprising contacting the starting material with at least one catalyst as defined in claim 1.

8. The method of claim 7, wherein the starting material comprises triglycerides, diglycerides, monoglycerides, fatty acids, esters of fatty acids, biomass derived biooils, ketone, alcohol or a combination thereof.

9. The method of claim 7, wherein the starting material is vegetable oil, used cooking oil, derived from animal fat, tall oil or any combination thereof.

10. The method of claim 7, wherein the starting material is diluted with a hydrocarbon or co-fed with a hydrocarbon or methanol or water or a hydrogen donor.

11. The method of claim 10, wherein the hydrogen donor is formic acid, methyl formate, methanol, ethanol, propanol, butanol, or any other suitable hydrogen donor agents or any combination thereof.

12. The method of any one of claim 7, wherein the deoxygenation reaction is conducted in the absence of added hydrogen or in the presence of added hydrogen.

13. The method of claim 7, wherein the deoxygenation reaction is conducted at a temperature between about 250° C. and about 500° C.

14. The method of claim 7, wherein the deoxygenation reaction is conducted at a pressure between about ambient pressure and about 5,000 psi.

15. The method of claim 7, wherein the deoxygenation reaction is conducted at a weight hourly space velocity between about 0.09 hr$^{-1}$ and about 3 hr$^{-1}$.

16. The method of claim 7, wherein at least one hydrocarbon product is produced.

17. The method of claim 16, wherein the at least one hydrocarbon product comprises one or more of alkanes, iso-alkanes, cycloalkanes, cycloolefins, aromatics, alkyl-aromatics, poly-aromatics, naphthenes, indanes or any combination thereof.

18. The method of claim 16, wherein the at least one hydrocarbon product is fractioned into gasoline, jet fuel, diesel and marine fuel boiling range or higher boiling hydrocarbons.

19. The method of claim 7, wherein a conversion efficiency of the deoxygenation reaction of the starting material is at least 20%.

20. The method of claim 7, wherein the deoxygenation reaction comprises at least one of a decarboxylation reaction, decarbonylation reaction and a dehydration reaction.

21. The method of claim 7, wherein a conversion efficiency of the deoxygenation reaction of the starting material is at least 90%.

\* \* \* \* \*